United States Patent
Otsuka et al.

(10) Patent No.: US 6,881,870 B2
(45) Date of Patent: Apr. 19, 2005

(54) PROCESS FOR PRODUCING ADAMANTANOL AND ADAMANTANONE

(75) Inventors: Kiyoshi Otsuka, Saitama (JP); Ichiro Yamanaka, Tokyo (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 0 days.

(21) Appl. No.: 10/480,654

(22) PCT Filed: Jun. 24, 2002

(86) PCT No.: PCT/JP02/06277

§ 371 (c)(1),
(2), (4) Date: Dec. 29, 2003

(87) PCT Pub. No.: WO03/002496

PCT Pub. Date: Jan. 9, 2003

(65) Prior Publication Data

US 2004/0199022 A1 Oct. 7, 2004

(30) Foreign Application Priority Data

Jun. 29, 2001 (JP) .......................................... 2001-197733

(51) Int. Cl.[7] .......................... C07C 35/37; C07C 35/22; C07C 45/32

(52) U.S. Cl. ...................... 568/818; 568/338; 568/357; 568/359; 568/360

(58) Field of Search ................................. 568/818, 338, 568/357, 359, 360

(56) References Cited

FOREIGN PATENT DOCUMENTS

| | | |
|---|---|---|
| EP | 531 715 | 3/1993 |
| EP | 1 026 140 | 8/2000 |

*Primary Examiner*—Elvis O. Price
(74) *Attorney, Agent, or Firm*—Oblon, Spivak, McClelland, Maier & Neustadt, P.C.

(57) ABSTRACT

There is provided a process for producing adamantanol and adamantanone which comprises reacting adamantane and oxygen in the presence of an oxidation catalyst constituted of a rare earth metal salt and a promoter containing an element selected from group 4 to group 10 of the new Periodic Table, and it is made possible through the production process according to the present invention to produce 2-adamantanol and 2-adamantanone in a high selectivity, high efficiency and safety by oxidizing adamantane under a mild reaction condition.

4 Claims, No Drawings

US 6,881,870 B2

PROCESS FOR PRODUCING ADAMANTANOL AND ADAMANTANONE

TECHNICAL FIELD

The present invention relates to a process for selectively producing adamantanol and adamantanone that are each an important intermediate of starting raw material for a variety of pharmaceuticals, agrochemicals and industrial products among adamantane derivatives by means of oxidization of adamantane.

BACKGROUND ART

Adamantane is known as a highly symmetrical cage compound which has a chemical constitution same as the constitution unit of diamond. Adamantane as a chemical substance is characterized by its (1) low energy of molecular strain and excellent heat resistance, (2) high dissolvability of fat and oil due to high carbon density, (3) less odor in spite of its sublimation properties and the like. Accordingly, attention has been paid since 1980 age to its availability in pharmaceutical field for raw materials of therapeutic drug for parkinsonism and therapeutic drug for influenza. Moreover in recent years, the characteristics such as heat resistance and transparency that are imparted to adamantane derivatives have attracted special attention in the fields of optical material such as photoresist for semiconductor production, magnetic recording medium, optical fiber, optical lens and optical disc substrate material; functional materials such as heat resistant plastics, coating material and adhesive; cosmetics; lubricating oil and the like, thereby expanding the application of the adamantane derivatives. In addition, the demands thereof have increased in the field of pharmaceuticals such as raw materials for anticancer drug, cerebral function-improving agent, therapeutic drug for neurological disorder and antiviral drug.

The technology of converting a hydrocarbon compound into an alcohol and a ketone through oxidation is technology of extreme industrial importance from the viewpoint of effective utilization of carbon resources. Although there has been industrially applied technology of producing an alcohol and a ketone from a monocyclic aliphatic compound such as cyclohexane, there has not yet been developed any technology of selectively efficiently producing a monohydric alcohol and a ketone through selective oxidation of a polycyclic aliphatic compound bearing secondary or tertiary carbon atoms.

In recent years, 2-adamantanol and 2-adamantanone from among adamantane derivatives have come to be spotlighted each as an important intermediate of a variety of pharmaceuticals and functional materials. However in the case of producing an alcohol by reacting adamantane with an oxidizing agent, the tertiary carbon atoms present in four numbers in one molecule thereof predominantly react to form not only a monohydric alcohol but also a dihydric alcohol and a trihydric alcohol, thereby making it impossible to selectively produce 2-adamantanol. In addition, 2-adamantanone is produced only by a process in which adamantane is heated and reacted in concentrated sulfuric acid.

As technology of producing adamantanol by oxidizing adamantane, there is known the technology in which adamantane is oxidized with oxygen in the presence of an imide compound (such as N-hydroxyphthalimide or the like) as a catalyst and a transition metal complex as a promoter {refer to Japanese Patent Application Laid-Open No. 327626/1997 (Heisei 9)}. Nevertheless, this technology suffers from low selectivity to a monohydric alcohol.

Further as technology of producing an oxocompound derivative (such as ketone), there is disclosed the catalytic technology in which a strong acid is added to the above-mentioned phthalimide compound as a catalyst and a transition metal complex as a promoter {refer to Japanese Patent Application Laid-Open No. 309469/1998 (Heisei 10)}. However, this technology suffers from low selectivity to the objective product and besides the formation of unfavorable byproducts such as 1-hydroxyadamantanone, 1-adamantanone, 1,3-adamantanediol and adamantanediol.

On the other hand, as technology other than the use of the above-mentioned phthalimide based catalyst, there is known a process for producing an alcohol and a ketone which comprises reacting adamantane in the presence of a transition metal complex having a porphyrin based organic compound as a ligand and of an aldehyde analogue {refer to Japanese Patent Application Laid-Open No. 87216/1997 (Heisei 9)}. Nevertheless, this process involves such problems as extremely low yield of adamantanol as low as 4.6% and 2-adamantanone as low as 0.7%, low selectivity to the objective products and besides the necessity for the coexistence of an expensive aldehyde analogue as a reducing agent.

In addition, there is reported a process for producing adamantanol which comprises hydroxylating an adamantane analogue in the presence of a ruthenium compound and hypochlorous acid or a salt thereof (refer to Japanese Patent Application Laid-Open No. 219646/2000). However, it is impossible for this process to selectively produce the objective 2-adamantanol, since the principal alcohol products are 1-adamantanol and 1,3-diadamantanol.

As technology for selectively producing 2-adamantanol, there is publicly well known a process for experimentally producing the same in concentrated sulfuric acid. For instance, it is reported by Schlatmann that 2-adamantanol is obtained at a yield of 72% by maintaining 1-adamantanol under heating at 30° C. for 12 hours in concentrated sulfuric acid {refer to Tetrahadronn: 24, 5361 (1968)}. There is proposed a process in which the reaction is put into practice under a two stage temperature condition as improved technology for the above-mentioned process wherein highly oxidative concentrated sulfuric acid is used also as a solvent {refer to Japanese Patent Application Laid-Open No. 189564/1999 (Heisei 11)}. Although this process enhances the yield of adamantanone, the problems still remain unsolved in that a large amount of concentrated sulfuric acid is used, thereby complicating the step of separation and refining after the reaction and at a the same time, necessitating the use of expensive and corrosion-resistant equipment and a material.

DISCLOSURE OF THE INVENTION

An object of the present invention is to provide a process which is capable of producing 2-adamantanol and 2-adamantanone in a high selectivity, high efficiency and safety by oxidizing adamantane under a mild reaction condition.

In such circumstances, intensive extensive research and investigation were accumulated by the present inventors in order to solve and eliminate the problems of the prior arts as mentioned hereinbefore and at the same time, produce 2-adamantanol and 2-adamantanone in a high selectivity, high efficiency and safety. As a result, it has been found that the above-mentioned object can be achieved by oxidizing adamantane in the presence of a specific oxidation catalyst. Thus the present invention has been accomplished on the basis of the foregoing findings and information.

Specifically, the present invention provides a process for producing adamantanol and adamantanone which comprises reacting adamantane and oxygen in the presence of an oxidation catalyst constituted of a rare earth metal salt and a promoter containing an element selected from group 4 to group 10 of the new Periodic Table.

THE MOST PREFERRED EMBODIMENT TO CARRY OUT THE INVENTION

As mentioned hereinabove, the oxidation catalyst to be used in the production process according to the present invention comprises a principal catalyst constituted of a rare earth metal salt and a promoter containing an element selected from group 4 to group 10 of the new Periodic Table (in particular, group IVA to VIIA and group VIII of the old Periodic Table).

The rare earth metal to be used therein is not specifically limited, but is exemplified preferably by europium, ytterbium, samarium and the like.

Examples of the rare earth metal salt preferably include a chloride of the above-mentioned rare earth metal and trifluoromethanesulfonium salt.

The amount of the principal catalyst to be used is at least 0.5 mol %, preferably at least 1.0 mol % based on adamantane as the reaction substrate. The amount to be used, when being less than 0.5 mol % based thereon, brings about failure in a sufficient reaction rate, whereas a larger amount thereof does not exert influence upon the reaction.

It is possible in the process according to the present invention to employ as a promoter, any of a variety of compounds containing an element selected from among group 4 to group 10 of the new Periodic Table. In particular, it is preferable that the catalyst system comprises an oxide complex containing an element selected from among titanium, cobalt, vanadium, chromium and manganese each belonging to any of group 4 to group 7 of the new Periodic Table, for instance, a titanium oxide complex; and a compound of a metal selected from among palladium, platinum, rhodium and nickel each belonging to any of group 8 to group 10 of the new Periodic Table, for instance, platinum oxide.

With regard to the promoter, the above-mentioned at least two kinds of compounds of a metal or metals may be used by being separately supported on each of catalyst carriers, or may be used as a composite carrier wherein the at least two kinds of compounds are supported in turn on one catalyst carrier. Examples of the aforesaid catalyst carriers include a porous carrier such as active carbon, zeolite, silica, silica-alumina and bentonite.

In the case where two kinds of compounds of a metal or metals is used, various combinations thereof are available, including for instance, preferable combination of titanium oxide-acetylacetonato complex and platinum oxide supported catalyst. In this case, the above-mentioned titanium oxide-acetylacetonato complex and platinum oxide supported catalyst each as a promoter may be used alone, or as a composite carrier wherein the titanium oxide-acetylacetonato complex is supported on the platinum oxide supported catalyst. The method of supporting metal species on a catalyst carrier is not specifically limited, but is exemplified by an ordinary impregnation method.

The amount of the promoter containing a metal or metals selected from among group 4 to group 7 of the new Periodic Table is at least 0.3 mol %, preferably at least 1.0 mol % based on adamantane as the reaction substrate. The amount to be used, when being less than 0.3 mol % based thereon, brings about failure in a sufficient reaction rate, whereas a larger amount thereof does not exert influence upon the reaction.

The amount of the promoter containing a metal or metals selected from among group 8 to group 10 of the new Periodic Table on the basis of active metal compound is at least 0.007 part by weight, preferably at least 0.010 part by weight each based on adamantane as the reaction substrate. The amount to be used, when being less than 0.007 part by weight based thereon, brings about failure in a sufficient reaction rate, whereas a larger amount thereof does not exert influence upon the reaction.

It is preferable in the production process according to the present invention to proceed with reaction by adding hydrogen as an activating agent for oxygen molecules to the reaction system, where hydrogen molecules are utilized as activating reducing agent for the oxygen molecules.

The reaction solvent to be used therein is not specifically limited provided that it does not react with hydrogen and oxygen and at the same time, adamantane is soluble therein, and is exemplified by acetic acid and ethyl acetate as a usable reaction solvent.

The amount of the reaction solvent to be used is 1 to 300 parts by weight, preferably 3 to 200 parts by weight each based on 1 part by weight of adamantane. An amount thereof to be used, when being less than 1 part by weight based thereon, sometimes gives rise to deposit of adamantane as the reaction substrate, whereas an amount thereof, when being more than 300 parts by weight based thereon, leads to lowered reaction rate.

In addition, hydrogen and oxygen are supplied to the reaction system each in the form of gas under atmospheric pressure. The supply ratio of oxygen/hydrogen is in the range of 0.1 to 10, preferably 1 to 3. A ratio thereof, when being less than 0.1, allows a side reaction of forming water to proceed, whereas a ratio thereof, when being more than 10, brings about a marked decrease in reaction rate.

Further, the reaction temperature is in the range of 0 to 110° C., preferably 30 to 80° C. The reaction time is in the range of 0.5 to 5 hours, preferably 1 to 3 hours.

EXAMPLES

In what follows, the present invention will be described in more detail with reference to comparative examples and working examples, which however shall never limit the present invention thereto.

The hydrogen activation promoters which were used in the following working examples were each prepared by impregnating and supporting any of various metals each of which belonged mainly to a noble metal and had hydrogen dissociation/adsorption function into and on a carrier, and then subjecting the metal to a firing or reducing treatment. In the following, some description will be given as typical examples, of methods for preparing a catalyst ($PtO_x/SiO_2$) wherein platinum was supported on silica as the carrier and a composite catalyst $\{(TiO(acac)_z/PtO_x/SiO_2\}$ wherein acac denotes acetyl acetonato.

Reference Example 1
{Preparation of 1 wt %-$PtO_x/SiO_2$ (SIO-8) promoter}

To 850 milliliter (mL) of ion exchange water in a 300 mL of a beaker was added 4950 g of $SiO_2$ (Reference Catalyst JRC-SIO-8 of The Institute of Catalyst), and 13.4 mL of 1.91 mol/liter of aqueous solution of H$_2$PtCl$_4$ was added dropwise in the beaker by means of a burette under heating and stirring. The resultant mixture was evaporated to bone dryness under vigorous stirring, further sufficiently dried and thereafter, fired in a muffle furnace at 150° C. for 2 hours subsequently at 300° C. for 4 hours to obtain PtO$_x$/SiO$_2$ (SIO-8) promoter.

Reference Example 2
{Preparation of TiO(acac)$_2$/PtO$_x$/SiO$_2$ catalyst}

To 20 mL of acetic acid in a 100 mL of a beaker was added 20 μmol of TiO(acac)$_2$ under heating and stirring to completely dissolve it. Thereafter 500 mg of 1 wt %-PtO$_x$/SiO$_2$ which had been prepared in advance was added in the beaker. The resultant mixture was evaporated to bone dryness on a hot plate at 150° C. under vigorous stirring, and further sufficiently dried. Thereafter, the dried product was used for the reaction as such without treatment in particular. In the following, the reaction was put into practice by varying the amount of the titanium oxide acetyl acetonato {TiO(acac)$_2$} to be added in accordance with the amount of the titanium oxide acetyl acetonato to be supported.

Example 1

A 100 mL of three neck round bottom flask which had been equipped with a stirrer, a thermometer and a Dimroth condenser was charged with 0.136 g (1 mmol), 1.29 mg (5 μmol) of europium chloride, 0.86 mg (3.3 μmol) of titanium oxide acetyl acetonato each as the catalyst, 0.1 g of platinum oxide supported catalyst and 20 mL of acetic acid as the solvent to proceed with the reaction at 40° C. for 2 hours, while passing a mixed gas of hydrogen and oxygen through the flask at a flow rate of 20 mL/min at a hydrogen partial pressure of 75.9 kPa and an oxygen partial pressure of 25.4 kPa.

After the completion of the reaction, the produced liquid was analyzed by means of gas chromatogram (available from Shimadzu GC-14A column, PEG=20 M, capillary column). As a result, there were obtained as the objective products, 93.8 μmol of 1-adamantanol, 22.2 μmol of 2-adamantanone and 75.7 μmol of 2-adamantanol at a yield of 19.2% with selectivity to 2-adamantanone and 2-adamantanol of 51.1%. The performance results are given in Table 1.

Example 2

The procedure in Example 1 was repeated to prepare the products except that europium chloride was used in an amount of 2.59 mg (10 μmol). The results are given in Table 1.

Example 3

The procedure in Example 1 was repeated to prepare the products except that europium chloride was used in an amount of 5.17 mg (20 μmol). The results are given in Table 1.

Example 4

The procedure in Example 1 was repeated to prepare the products except that europium chloride was used in an amount of 15.51 mg (60 μmol). The results are given in Table 1.

Example 5

The procedure in Example 1 was repeated to prepare the products except that europium chloride was used in an amount of 31.02 mg (120 μmol). The results are given in Table 1.

Example 6

The procedure in Example 2 was repeated to prepare the products except that titanium oxide acetyl acetonato was used in an amount of 5.24 mg (20 μmol). The results are given in Table 1.

Example 7

The procedure in Example 3 was repeated to prepare the products except that titanium oxide acetyl acetonato was used in an amount of 5.24 mg (20 mol). The results are given in Table 1.

Example 8

The procedure in Example 4 was repeated to prepare the products except that titanium oxide acetyl acetonato was used in an amount of 5.24 mg (20 μmol). The results are given in Table 1.

Example 9

The procedure in Example 6 was repeated to prepare the products except that titanium oxide acetyl acetonato was used in an amount of 31.02 mg (120 μmol). The results are given in Table 1.

Example 10

The procedure in Example 9 was repeated to prepare the products except that adamantane and titanium oxide acetyl acetonato were used in amounts of 0.272 g (2 mmol) and 0.86 mg (3.3 μmol), respectively. The results are given in Table 1.

Example 11

The procedure in Example 9 was repeated to prepare the products except that adamantane was used in an amount of 0.272 g (2 mmol). The results are given in Table 1.

Example 12

The procedure in Example 1 was repeated to prepare the products except that use was made of 0.1 g of platinum oxide catalyst supporting 20 μmol of titanium oxide acetyl acetonato. The results are given in Table 1.

Example 13

The procedure in Example 1 was repeated to prepare the products except that use was made of 0.1 g of platinum oxide catalyst supporting 3.3 μmol of titanium oxide acetyl acetonato. The results are given in Table 1.

Comparative Example 1

The procedure in Example 1 was repeated to prepare the products except that europium chloride was not used in the reaction. The results are given in Table 1.

Comparative Example 2

The procedure in Example 6 was repeated to prepare the products except that europium chloride was not used in the reaction. The results are given in Table 1.

Comparative Example 3

The procedure in Example 1 was repeated to prepare the products except that europium chloride and titanium oxide acetyl acetonato were not used in the reaction. The results are given in Table 1.

Comparative Example 4

The procedure in Example 3 was repeated to prepare the products except that titanium oxide acetyl acetonato was not used in the reaction. The results are given in Table 1.

Comparative Example 5

The procedure in Example 3 was repeated to prepare the products except that a hydrogen activation promoter was not used in the reaction. The results are given in Table 1.

TABLE 1

| | Charge | | | | |
|---|---|---|---|---|---|
| | Adamantane (mmol) | EuCl$_3$ ($\mu$mol) | TiO(acac)$_2$ ($\mu$mol) | PtOx/ SiO$_2$ (g) | TiO-(acac)$_2$/ PtOx/SiO$_2$ ($\mu$mol)/ (g) |
| Example 1 | 1 | 5 | 3.3 | 0.1 | — |
| Example 2 | 1 | 10 | 3.3 | 0.1 | — |
| Example 3 | 1 | 20 | 3.3 | 0.1 | — |
| Example 4 | 1 | 60 | 3.3 | 0.1 | — |
| Example 5 | 1 | 120 | 3.3 | 0.1 | — |
| Example 6 | 1 | 10 | 20 | 0.1 | — |
| Example 7 | 1 | 20 | 20 | 0.1 | — |
| Example 8 | 1 | 60 | 20 | 0.1 | — |
| Example 9 | 1 | 120 | 20 | 0.1 | — |
| Example 10 | 2 | 120 | 3.3 | 0.1 | — |
| Example 11 | 2 | 120 | 20 | 0.1 | — |
| Example 12 | 1 | 20 | — | — | 20/0.1 |
| Example 13 | 1 | 20 | — | — | 20/0.1 |
| Comparative Example 1 | 1 | 0 | 20 | 0.1 | 0.1 |
| Comparative Example 2 | 1 | 0 | 0 | 0.1 | 0.1 |
| Comparative Example 3 | 1 | 0 | 0 | 0.1 | 0.1 |
| Comparative Example 4 | 1 | 20 | 20 | 0.1 | 0.1 |
| Comparative Example 5 | 1 | 20 | 20 | 0 | — |

| | Reaction Performance | | | | |
|---|---|---|---|---|---|
| | Product ($\mu$mol) | | | Yield | |
| | 1 - OH | 2 - AdO | 2 - AdOH | (%) | Selectivity (%) |
| Example 1 | 93.8 | 22.2 | 75.7 | 19.2 | 51.1 |
| Example 2 | 114.7 | 36.6 | 81.2 | 23.2 | 50.6 |
| Example 3 | 151.6 | 75.9 | 71.1 | 29.9 | 49.2 |
| Example 4 | 157.2 | 108.3 | 56.4 | 32.2 | 51.2 |
| Example 5 | 158.3 | 136.0 | 47.2 | 34.1 | 53.6 |
| Example 6 | 147.4 | 57.9 | 74.4 | 28 | 47.3 |
| Example 7 | 152.2 | 72.7 | 66.5 | 29.1 | 47.8 |
| Example 8 | 179.9 | 129.7 | 54.5 | 36.4 | 50.6 |
| Example 9 | 162.0 | 149.3 | 38.7 | 35 | 53.7 |
| Example 10 | 261.7 | 104.0 | 121.3 | 24.3 | 46.3 |
| Example 11 | 350.0 | 215.4 | 87.2 | 32.6 | 46.4 |
| Example 12 | 168.8 | 86.2 | 63.5 | 31.9 | 47.0 |
| Example 13 | 165.6 | 76.0 | 89.5 | 33.1 | 50.0 |
| Comparative Example 1 | 9.3 | 20.0 | 8.4 | 1.8 | 47.5 |
| Comparative Example 2 | 22.2 | 5.7 | 10.8 | 3.9 | 42.6 |
| Comparative Example 3 | 1.8 | 0 | 1.0 | 0.3 | 36.3 |
| Comparative Example 4 | 11.5 | 0 | 12.4 | 2.4 | 51.9 |
| Comparative Example 5 | 0.8 | 0 | 0 | 0 | 0 |

{Remarks}
1-OH: 1-adamantanol, 2-AdO: 2-adamantanone, 2-AdOH: 2-adamantanol,
Yield = Amount of product ($\mu$mol)/charged raw material ($\mu$mol) × 100(%)
Selectivity = {Amount of produced 2-AdO ($\mu$mol) + (Amount of produced 2-AdOH ($\mu$mol)}/amount of product ($\mu$mol) × 100(%)

INDUSTRIAL APPLICABILITY

According to the production process of the present invention, it is made possible to produce in a high selectivity, high efficiency and safety, 2-adamantanol and 2-adamantanone that are useful in the fields of pharmaceuticals and agrochemicals, semiconductors, magnetic recording media, optical materials, heat resistant plastics, coating materials, adhesives, cosmetics, lubricating oils and the like by oxidizing adamantane under a mild reaction condition. In addition according to the production process of the present invention, since no corrosive substance is used in the reaction system, it is not necessary to use any expensive and corrosion-resistant equipment and a material and at the same time, the step of separation and refining after the reaction is simplified.

What is claimed is:

1. A process for producing adamantanol and adamantanone which comprises reacting adamantane and oxygen in the presence of an oxidation catalyst constituted of a rare earth metal salt and a promoter containing an element selected from group 4 to group 10 of the new Periodic Table.

2. The process for producing adamantanol and adamantanone according to claim 1, wherein the rare earth metal is europium, ytterbium or samarium which are each trivalent.

3. The process for producing adamantanol and adamantanone according to claim 1, wherein the promoter in the catalyst system comprises a compound of a metal selected from among titanium, cobalt, vanadium, chromium and manganese each belonging to any of group 4 to group 7 of the new Periodic Table, and a compound of a metal selected from among palladium, platinum, rhodium and nickel each belonging to any of group 8 to group 10 of the new Periodic Table.

4. The process for producing adamantanol and adamantanone according to claim 1, wherein hydrogen is added to reactants as an activating agent for oxygen molecules.

* * * * *

UNITED STATES PATENT AND TRADEMARK OFFICE
CERTIFICATE OF CORRECTION

PATENT NO. : 6,881,870 B1
DATED : March 1, 2005
INVENTOR(S) : Cheng et al.

It is certified that error appears in the above-identified patent and that said Letters Patent is hereby corrected as shown below:

Title page,
Item [30], Related U.S. Application Data, should read:
-- Continuation-in-part of application no. 10/133,106, filed on April 26, 2002. --.

Signed and Sealed this

Twenty-seventh Day of December, 2005

JON W. DUDAS
*Director of the United States Patent and Trademark Office*

UNITED STATES PATENT AND TRADEMARK OFFICE
CERTIFICATE OF CORRECTION

PATENT NO. : 6,881,870 B2
DATED : April 19, 2005
INVENTOR(S) : Kiyoshi Otsuka et al.

It is certified that error appears in the above-identified patent and that said Letters Patent is hereby corrected as shown below:

This certificate supersedes Certificate of Correction issued December 27, 2005, the number was erroneously mentioned and should be vacated since no Certificate of Correction was granted.

Signed and Sealed this

Thirty-first Day of January, 2006

JON W. DUDAS
*Director of the United States Patent and Trademark Office*